United States Patent

Hagihara et al.

[11] Patent Number: 5,547,591
[45] Date of Patent: Aug. 20, 1996

[54] METHOD FOR SEPARATING A BLOOD MATERIAL INTO BLOOD COMPONENTS BY CENTRIFUGATION, AND CENTRIFUGAL APPARATUS

[75] Inventors: Takeaki Hagihara, Oita; Maho Torii, Yokohama, both of Japan

[73] Assignee: Asahi Medical Co., Ltd., Tokyo, Japan

[21] Appl. No.: 251,954

[22] Filed: Jun. 1, 1994

[30] Foreign Application Priority Data

Jun. 1, 1993 [JP] Japan ................. 5-152641

[51] Int. Cl.$^6$ ............ B01D 21/26; B01D 35/00; B01D 35/02
[52] U.S. Cl. .............. 210/782; 1306/206; 1306/232; 1306/257.1; 1306/360.1; 1306/435; 1306/787; 494/36; 494/37; 604/406; 604/408; 604/410
[58] Field of Search .................. 210/767, 782, 210/787, 206, 360.1, 232, 361, 364, 365, 367, 435, 257.1; 494/33, 34, 36, 37; 604/406, 408, 409, 410

[56] References Cited

U.S. PATENT DOCUMENTS

| | | | |
|---|---|---|---|
| 4,596,657 | 6/1986 | Wisdom | 210/206 |
| 4,767,541 | 8/1988 | Wisdom | 210/749 |
| 4,810,378 | 3/1989 | Carmen et al. | 210/206 |
| 4,915,848 | 4/1990 | Carmen et al. | 210/749 |
| 4,919,823 | 4/1990 | Wisdom | 210/749 |
| 4,943,287 | 7/1990 | Carmen | 604/408 |
| 4,985,153 | 1/1991 | Kuroda et al. | 210/782 |
| 4,997,577 | 3/1991 | Stewart | 210/767 |
| 5,089,146 | 2/1992 | Carmen et al. | 210/782 |
| 5,092,996 | 3/1992 | Spielberg | 210/232 |
| 5,100,564 | 3/1992 | Pall et al. | 210/782 |

FOREIGN PATENT DOCUMENTS

| | | |
|---|---|---|
| 0402698 | 12/1990 | European Pat. Off. . |
| 0536594 | 4/1993 | European Pat. Off. . |
| 0591980 | 7/1993 | European Pat. Off. . |
| 4022700 | 7/1990 | Germany . |
| 9000059 | 1/1990 | WIPO . |
| 9104088 | 4/1991 | WIPO . |
| 9211059 | 7/1992 | WIPO . |
| 9220427 | 11/1992 | WIPO . |
| 9220428 | 11/1992 | WIPO . |

*Primary Examiner*—John Kim
*Attorney, Agent, or Firm*—Birch, Stewart, Kolasch & Birch, LLP

[57] ABSTRACT

Disclosed is a method for separating a blood material into blood components by centrifugation, wherein when a multiple blood bag unit including a plurality of flexible blood bags (at least one of the flexible blood bags containing a blood material) liquid-tightly connected to at least one leukocyte-removing filter device through flexible tubes in a predetermined order is accommodated in a centrifuge bucket, at least the blood material-containing flexible blood bag or bags are inserted in the centrifuge bucket while placing at least the leukocyte-removing filter device outside of the centrifuge bucket, wherein the leukocyte-removing filter device is directly or indirectly secured relative to the rotor and a center of the filter device is located at a distance from an axis of the rotation shaft which is smaller than a distance between a pivotal axis of the turning of the centrifuge bucket and an axis of the rotation shaft at a portion thereof which has the rotor connected thereto. A centrifugal apparatus for practicing the method is also disclosed. By the method and apparatus of the present invention, the centrifugal force to be sustained by the filter device is reduced to a minimum due to the location of the filter device at a reduced distance from the rotation shaft, so that the danger of damaging or adversely affecting the filter device due to the centrifugal force is extremely reduced or eliminated.

18 Claims, 5 Drawing Sheets

FIG. 1

PRIOR ART

METHOD FOR SEPARATING A BLOOD MATERIAL INTO BLOOD COMPONENTS BY CENTRIFUGATION, AND CENTRIFUGAL APPARATUS

BACKGROUND OF THE INVENTION

FIELD OF THE INVENTION

The present invention relates to a method for separating a blood material into blood components by centrifugation. More particularly, the present invention is concerned with a method for separating a blood material into blood components by centrifugation, wherein a multiple blood bag unit, which includes a plurality of flexible blood bags (at least one of the flexible blood bags containing a blood material) liquid-tightly connected to at least one leukocyte-removing filter device through flexible tubes in a predetermined order, is accommodated in a centrifuge bucket of a centrifugal apparatus in which the centrifuge bucket is swingably attached to a rotor fixedly connected to a rotation shaft, and the rotation shaft is rotated to rotate the rotor and turn and orient the centrifuge bucket in a direction of a centrifugal force exerted, thereby performing separation of the blood material into blood components by centrifugation, and wherein when the multiple blood bag unit is accommodated in the centrifuge bucket, at least the blood material-containing flexible blood bag or bags are inserted in the centrifuge bucket while placing at least the leukocyte-removing filter device outside of the centrifuge bucket, wherein the leukocyte-removing filter device is directly or indirectly secured relative to the rotor and a center of the filter device is located at a distance from an axis of the rotation shaft which is smaller than a distance between a pivotal axis of the turning of the centrifuge bucket and an axis of the rotation shaft at a portion thereof which has the rotor connected thereto.

The present invention is also concerned with a centrifugal apparatus for practicing the method of the present invention.

By the method and apparatus of the present invention, the centrifugal force to be sustained by the filter device is reduced to a minimum due to the location of the filter device at a reduced distance from the rotation shaft, so that the danger of damaging or adversely affecting the filter device due to the centrifugal force is extremely reduced or eliminated. Further, since the filter device is placed outside of the centrifuge bucket, the centrifuge bucket can have an enough room for accommodating the blood bags. Therefore, not only can insertion of the blood bags into and taking-out thereof from the centrifuge bucket be readily performed with no difficulty, but also, even when the filter device has an angular portion or a projection, there is no danger of damaging the filter device and the blood bags due to a pressure-contact of the angular portion or projection of the filter device with the blood bags.

DISCUSSION OF RELATED ART

In recent years, in accordance with the progress of immunology and study of transfusion, it has become clear that side effects of transfusion are caused by the leukocytes contained in a blood material used for transfusion. Side effects of transfusion include not only relatively mild side effects, such as headache, nausea, chilliness and nonhemolytic febrile transfusion reactions, but also serious side effects. With respect to the latter, particularly when a transfusion recipient has an immunopathy, transfusion is likely to cause serious side effects, such as graft versus host (GVH) reaction, in which transfused leukocytes attack the skin and internal organs of the recipient, infections by viruses present in the leukocytes, e.g., cytomegalovirus infection, and allosensitization. For effective prevention of such side effects of transfusion, it is now widely practiced to remove leukocytes from a blood material by means of a leukocyte-removing filter device having a non-woven fabric, a porous element and/or the like packed therein.

On the other hand, recently, a blood material to be used for transfusion is not limited to whole blood, and there is a strong demand for blood components, such as a red cell concentrate, plasma and a platelet concentrate.

Therefore, it is usually required that a blood material to be used for transfusion be a blood component from which leukocytes have been removed. Such a leukocyte-removed blood component can be obtained by, for example, collecting a blood material, such as whole blood, from a donor, removing leukocytes from the blood material, and centrifuging the resultant leukocyte-removed blood product to thereby separate it into blood components. (The removal of leukocytes may be conducted after the centrifugation.) It is required that these operations be conducted readily under aseptic conditions.

For use in conducting these operations effectively and efficiently under aseptic conditions, various types of multiple blood bag units containing a leukocyte-removing filter have been proposed which can be used for aseptically removing leukocytes from a blood material immediately after the collection of the blood material (see, for example, U.S. Pat. Nos. 4,596,657 and 4,985,153).

Each of these multiple blood bag units generally comprises a primary bag (blood collection bag); a leukocyte-removing filter device liquid-tightly connected to an outlet of the primary bag through a flexible tube; and at least one satellite bag liquid-tightly connected to an outlet of the filter device through a flexible tube. Each of the primary bag and the satellite bag is made of a flexible material, such as polyvinyl chloride. The leukocyte-removing filter device comprises a casing having an inlet and an outlet and a filter material disposed in the casing. The casing is made of a relatively rigid material, such as a polycarbonate, and the filter material is comprised of, for example, a non-woven fabric or a porous element. Such a multiple blood bag unit is generally called a unit of a "closed system".

A blood material collected in a multiple blood bag unit is subjected to centrifugation, using a centrifugal apparatus, so that the blood material is separated into a plasma layer (containing or not containing platelets depending on the centrifugation conditions) and a red cell concentrate layer. In this case, when a centrifugation of the blood material is to be performed for separating the blood material into blood components while keeping asepsis, it is necessary that the entire multiple blood bag unit be subjected to centrifugation.

Figure 1:
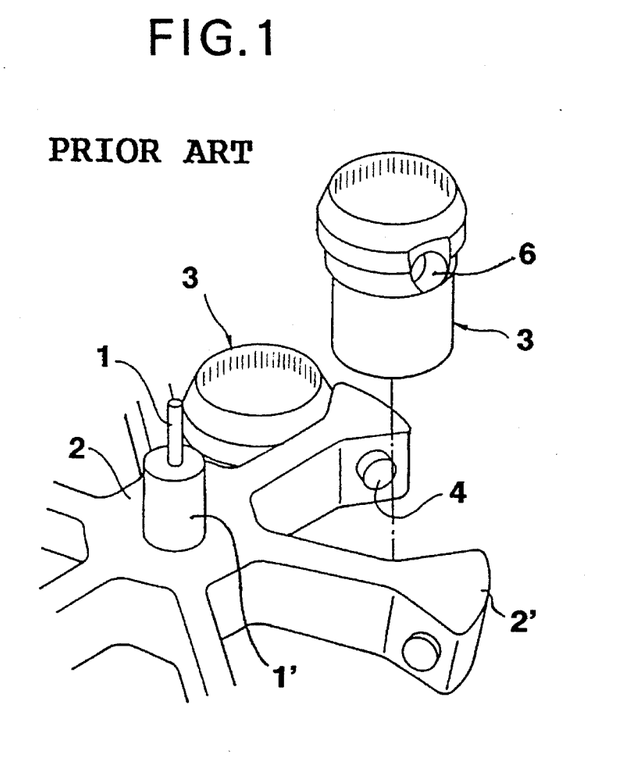
FIG. 1 is a partly cut-away diagrammatic perspective view of a conventional centrifugal apparatus for separating a blood material into blood components, showing main portions thereof.

FIG. 1 is a partly cut-away diagrammatic perspective view of a conventional centrifugal apparatus, showing main portions of the apparatus. As shown in FIG. 1, the conventional centrifugal apparatus for use in separating a blood material into blood components has rotation shaft 1 (having cylindrical reinforcing member 1' provided therearound and secured thereto by means of, for example, an adhesive) to be connected to a drive motor (not shown), and a rotor fixedly connected at a central portion thereof to rotation shaft 1 through engagement between a threaded periphery of rotation shaft 1 and a threaded inner wall of the central bore of the rotor in a manner such that the connection therebetween is not loosened during centrifugation. The rotor comprises central body portion 2 and a plurality of arms 2' which are substantially equal in length and radially extend from central body portion 2 at appropriate intervals allowing the center of gravity of the rotor to be positioned at a geometrical center (rotation center) of the rotor during rotation of the rotor including the arms. The centrifugal apparatus also has centrifuge buckets 3 each for accommodating therein a multiple blood bag unit (not shown), and each bucket 3 is swingably attached to the rotor by means of a pair of pivot pins 4, 4 extending laterally of the arms and pivot pin-receiving recesses 6, 6 formed in opposite sides of bucket 3, so that bucket 3 is individually, pivotally held between neighboring arms 2', 2'. Bucket 3 is adapted to be turned and oriented in a direction of the centrifugal force exerted when the rotor is rotated.

A leukocyte-removing filter device having a filter material (such as a non-woven fabric and a porous element) disposed therein has a very delicate structure. When a multiple blood bag unit including such a filter device is accommodated in a centrifuge bucket and subjected to centrifugation, the bulk density of a non-woven fabric as a filter material or the pore diameter of a porous element as a filter material is likely to undesirably change due to the centrifugal force. Further, there is a danger that the filter device is pushed against a bottom floor of the centrifuge bucket due to the centrifugal force, thereby leading to a damage to the filter device and/or a breakage of flexible connecting tubes.

Generally, commercially available centrifuge buckets, such as one used in the conventional centrifugal apparatus as shown in FIG. 1, have originally been designed for use along with a multiple blood bag unit of a non-closed system, which includes only flexible components, such as blood bags and flexible tubes connecting the blood bags, and does not include a filter device. In such a non-closed system, removal of leukocytes from a blood material is conducted using a filter device provided separately from the multiple blood bag unit. Therefore, the commercially available centrifuge buckets do not have satisfactorily enough rooms for accommodating therein a multiple blood bag unit of a closed system which contains a leukocyte-removing filter device (having a relatively rigid casing) in addition to flexible components (such as flexible blood bags and flexible connecting tubes), so that it is difficult and time-consuming to accommodate the entire closed system into the centrifuge bucket. Further, due to the stress sustained by the closed system when squeezing it into the bucket, there is a danger that the closed system suffers a damage during the accommodation thereof into the bucket.

In order to solve the above problems, U.S. Pat. No. 5,100,564 discloses the use of a support means (referred to as "bracket" in the above mentioned U.S. Patent) which is provided so as to engage the upper circumference of a centrifuge bucket and which supports a flat, disk-like filter thereon under the centrifugal force. In U.S. Pat. No. 5,100, 564, when a multiple blood bag unit is to be placed in the centrifuge bucket, the blood bags are first placed in the centrifuge cup and then the support means is placed so as to engage the upper circumference of the centrifuge cup, and subsequently the filter is set on the support means so that both sides of the disk-like filter are at right angles relative to a depthwise direction of the centrifuge bucket. The disk-like filter has a blood inlet nozzle and a blood outlet nozzle which protrude outwardly of both sides of the filter, and the support means has slots for fittedly receiving the inlet and outlet nozzles of the filter. If the technique of the above U.S. Patent can be practically employed, since the filter is placed at the top of the centrifuge bucket, i.e., near a rotation shaft of a centrifugal apparatus, a centrifugal force to be sustained by the filter can be decreased, as compared to that to be sustained by a filter placed inside of the bucket.

However, the above-mentioned support means (bracket) disclosed in U.S. Pat. No. 5,100,564 needs to be designed to engage the upper circumference of the centrifuge bucket. The support means also has to have a configuration which can fittedly receive the inlet and outlet nozzles of the filter. That is, the use of the support means is extremely limited in that the support means has to be specially designed in accordance with the structures of the centrifuge bucket and the filter. Commercially available centrifuge buckets vary in size and shape, and examples of shapes thereof include a cylinder, a hollow structure having an elliptic cross-section and a hollow structure having an elliptic cross-section and containing an internal space partitioned into a plurality of cylindrical chambers. Furthermore, there are various commercially available leukocyte-removing filters varying in shape, such as a disk-like filter having inlet and outlet nozzles in both sides of a disk-like casing, and a flat square filter having inlet and outlet nozzles located at opposite ends of the casing, and a flat elliptic filter having inlet and outlet nozzles located at opposite ends of the casing.

Further, as shown in FIGS. 2(a) to 6 illustrating various forms of the centrifugal apparatus which can be used in the method of the present invention, a blood bag to be accommodated in a centrifuge bucket has flexible tubes connected to an upper end thereof. The height of a blood bag with flexible tubes connected to an upper end portion of the blood bag is usually larger than the depth of the centrifuge bucket, so that when a blood bag having flexible tubes connected thereto is accommodated in a centrifuge bucket, the upper end portion of the blood bag protrudes outside of the opening of the centrifuge bucket. Therefore, when the support means disclosed in U.S. Pat. No. 5,100,564 is placed so as to engage the upper circumference of the centrifuge bucket, the support means is pushed upwards by the upper end portions of the blood bags protruding outside of the opening of the centrifuge bucket, so that it is frequently impossible to ensure that the support means fittedly and stably engages the upper circumference of the centrifuge bucket. When the support means does not fittedly and stably engage the upper circumference of the centrifuge bucket, there is a danger that the support means is released from the centrifuge bucket and is out of the centrifuge bucket together with the filter device during centrifugation, or the support means falls into the centrifuge bucket together with the filter device during centrifugation. It is possible to forcibly engage the support means to the upper circumference of the centrifuge bucket by means of an adhesive tape or the like. However, not only is this operation itself cumbersome, but also there is a danger that the connecting portions of the blood bag with the flexible tubes at the upper end of the blood bag are damaged by the support means which is pushed against the upper end of the blood bag.

SUMMARY OF THE INVENTION

The present inventors have made extensive and intensive studies with a view toward developing a novel method for separating a blood material into blood components by centrifugation, which is free from the above-mentioned problems inevitably accompanying the conventional methods. As a result, it has unexpectedly been found that the above-mentioned problems can be solved by a novel method for separating a blood material into blood components by centrifugation, wherein a multiple blood bag unit, which includes a plurality of flexible blood bags (at least one of the flexible blood bags containing a blood material) liquid-tightly connected to at least one leukocyte-removing filter device through flexible tubes in a predetermined order, is accommodated in a centrifuge bucket of a centrifugal apparatus in which the centrifuge bucket is swingably attached to a rotor fixedly connected to a rotation shaft, and the rotation shaft is rotated to rotate the rotor and turn and orient the centrifuge bucket in a direction of a centrifugal force exerted, thereby performing separation of the blood material into blood components by centrifugation, and wherein when the multiple blood bag unit is accommodated in the centrifuge bucket, at least the blood material-containing flexible blood bag or bags are inserted in the centrifuge bucket while placing at least the leukocyte-removing filter device outside of the centrifuge bucket, wherein the leukocyte-removing filter device is directly or indirectly secured relative to the rotor and a center of the filter device is located at a distance from an axis of the rotation shaft which is smaller than a distance between a pivotal axis of the turning of the centrifuge bucket and an axis of the rotation shaft at a portion thereof which has the rotor connected thereto. The present inventors have also developed a novel centrifugal apparatus which can advantageously be used for practicing the above method.

By the method and apparatus of the present invention, the centrifugal force to be sustained by the filter device is reduced to a minimum due to the location of the filter device at a reduced distance from the rotation shaft, so that the danger of damaging or adversely affecting the filter device due to the centrifugal force is extremely reduced or eliminated. Further, since the filter device is placed outside of the centrifuge bucket, the centrifuge bucket can have an enough room for accommodating the blood bags. Therefore, not only can insertion of the blood bags into and taking-out thereof from the centrifuge bucket be readily performed with no difficulty, but also, even when the filter device has an angular portion or a projection, there is no danger of damaging the filter device and the blood bags due to a pressure-contact of the angular portion or projection of the filter device with the blood bags. Moreover, since the blood bags can be readily taken out from the centrifuge bucket after the centrifugation operation with no difficulty, it is unlikely that the blood components of the blood material, which have been once separated by the centrifugation, are mixed.

Based on the above novel findings, the present invention has been completed.

Accordingly, it is an object of the present invention to provide a novel method for separating a blood material into blood components by centrifugation, in which not only can the danger of damaging or adversely affecting the filter device of a multiple blood bag unit during centrifugation be eliminated by effectively reducing to a minimum the centrifugal force to be sustained by the filter device, but also insertion of the blood bags into and taking-out thereof from the centrifuge bucket can be readily performed and, even when the filter device has an angular portion or a projection, there is no danger of damaging the filter device and the blood bags due to a pressure-contact of the angular portion or projection of the filter device with the blood bags.

It is another object of the present invention to provide a novel centrifugal apparatus for centrifuging a blood material collected in a multiple blood bag unit to thereby separate the blood material into blood components, which can be advantageously employed for practicing the method of the present invention.

The foregoing and other objects, features and advantages of the present invention will be apparent to those skilled in the art from the following detailed description and appended claims taken in connection with the accompanying drawings.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

In the accompanying drawings:

In FIG. 1 through FIG. 6, like parts or portions are designated by like numerals and characters.

DETAILED DESCRIPTION OF THE INVENTION

According to the present invention, there is provided a method for separating a blood material into blood components by centrifugation, comprising the steps of:

(1) providing at least two multiple blood bag units each including a plurality of flexible blood bags liquid-tightly connected to at least one leukocyte-removing filter device through flexible tubes in a predetermined order, at least one of the flexible blood bags containing a blood material, and providing a centrifugal apparatus including a rotation shaft connected to a drive motor, a rotor fixedly connected at a central portion thereof to the rotation shaft and rotatable in accordance with rotation of the rotation shaft, the rotor including a central body portion and at least two centrifuge bucket-holding extensions radially extending from the central body portion, and at least two centrifuge buckets each swingably attached to the centrifuge bucket-holding extensions of the rotor, wherein the centrifuge bucket is adapted to be turned and oriented substantially in a direction of a centrifugal force exerted when the rotor is rotated;

(2) inserting at least the blood material-containing flexible blood bag of the plurality of flexible blood bags of each multiple blood bag unit in each centrifuge bucket while placing at least the leukocyte-removing filter device outside of the centrifuge bucket, wherein the filter device is directly or indirectly secured relative to the rotor, and wherein a center of each filter device is located at a distance from an axis of the rotation shaft which is smaller than a distance between a pivotal axis of the turning of the centrifuge bucket and an axis of the rotation shaft at a portion thereof which has the rotor connected thereto; and (3) actuating the drive motor to rotate the rotation shaft and the rotor and perform separation of the blood material in the blood bag into blood components by centrifugation.

Hereafter, the method of the present invention and the apparatus of the present invention will be described in detail.

In step (1) of the method of the present invention, at least two multiple blood bag units are provided. As shown in FIG. 2(a) through FIG. 6, each multiple blood bag unit to be used in the method of the present invention includes a plurality of flexible blood bags (a) liquid-tightly connected to at least one leukocyte-removing filter device (b) through flexible tubes (c) in a predetermined order, at least one of the flexible blood bags containing a blood material (not shown), such as whole blood. The blood material generally contains leukocytes. The blood bag containing the blood material may also contain an anticoagulant mixed with the blood material. The leukocyte-removing filter device (b) of the multiple blood bag unit generally comprises a casing having a blood inlet and a blood outlet, and a filter material disposed in the casing and communicated on one side thereof to the blood inlet and on the other side thereof to the blood outlet. With respect to the configuration and structure of the filter device of the multiple blood bag unit to be used in the present invention, there is no particular limitation.

In the present invention, various customary multiple blood bag units can be employed. Examples of customary multiple blood bag units employable in the present invention include those disclosed in U.S. Pat. Nos. 4,596,657, 4,767,541, 4,919,823, 4,810,378, 4,915,848, 5,092,996, 5,100,564, 5,089,146, 4,985,153, and 4,997,577, WO 92/20427, WO 92/20428, WO 91/04088, and German Patent Application Publication 4022700 A1. With respect to the manner of connection among the filter device and the blood bags through flexible tubes, reference can be made to these patent documents.

In the present invention, it is preferred to use a filter device comprising a casing having a blood inlet and a blood outlet which are both located in a top portion of the casing, as shown in FIGS. 2(a) through 6. With respect to a filter device in which both the inlet and outlet are located on the top portion of the filter device, reference can be made to copending U.S. patent application Ser. No. 08/132,894 and European Patent Application Publication No. 0 591 980 A2.

In step (1) of the method of the present invention, also a centrifugal apparatus is provided. The centrifugal apparatus to be used in the method of the present invention includes a rotation shaft (1) connected to a drive motor (not shown), and a rotor fixedly connected at a central portion thereof to the rotation shaft (1) and rotatable in accordance with rotation of the rotation shaft (1). The fixed connection between the rotor and the rotation shaft (1) is made through thread-engagement techniques ordinarily used in the art, e.g., through engagement between a threaded periphery of the rotation shaft (1) and a threaded inner wall of the central bore of the rotor in a manner such that the connection therebetween is not loosened during centrifugation. The rotor includes a central body portion (2) and at least two centrifuge bucket-holding extensions (2') radially extending from the central body portion (2), and at least two centrifuge buckets (3) each swingably attached to the centrifuge bucket-holding extensions (2') of the rotor. The centrifuge bucket (3) is adapted to be turned and oriented substantially in a direction of a centrifugal force exerted when the rotor is rotated.

In step (2) of the method of the present invention, at least the blood material-containing flexible blood bag or bags of the plurality of flexible blood bags (a) of each multiple blood bag unit are inserted in each centrifuge bucket (3) while placing at least the leukocyte-removing filter device (b) outside of the centrifuge bucket (3). The leukocyte-removing filter device (b) is directly or indirectly secured relative to the rotor. A center of each filter device (b) is located at a distance from an axis of the rotation shaft (1) which is smaller than a distance between a pivotal axis (7) of the turning of the centrifuge bucket (3) and an axis of the rotation shaft (1) at a portion thereof which has the rotor connected thereto.

Figure 2A:
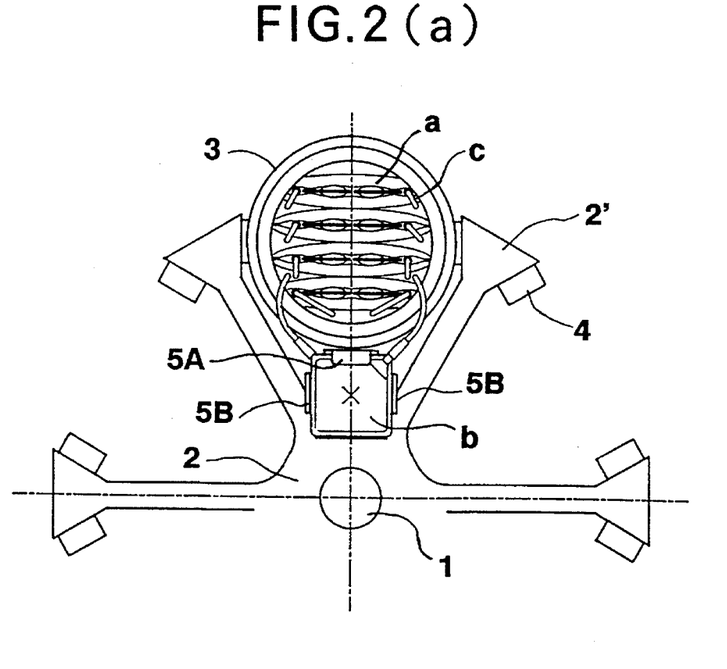
FIG. 2(a) is a partly cut-away diagrammatic plan view of one form of the centrifugal apparatus of the present invention, showing main portions thereof, which can be used in the method of the present invention, shown with a multiple blood bag unit inserted in a centrifuge bucket swingably held between neighboring arms of the rotor, and shown with a leukocyte-removing filter device placed outside of the centrifuge bucket and secured to the rotor by means of a filter device-securing means.
Figure 3A:
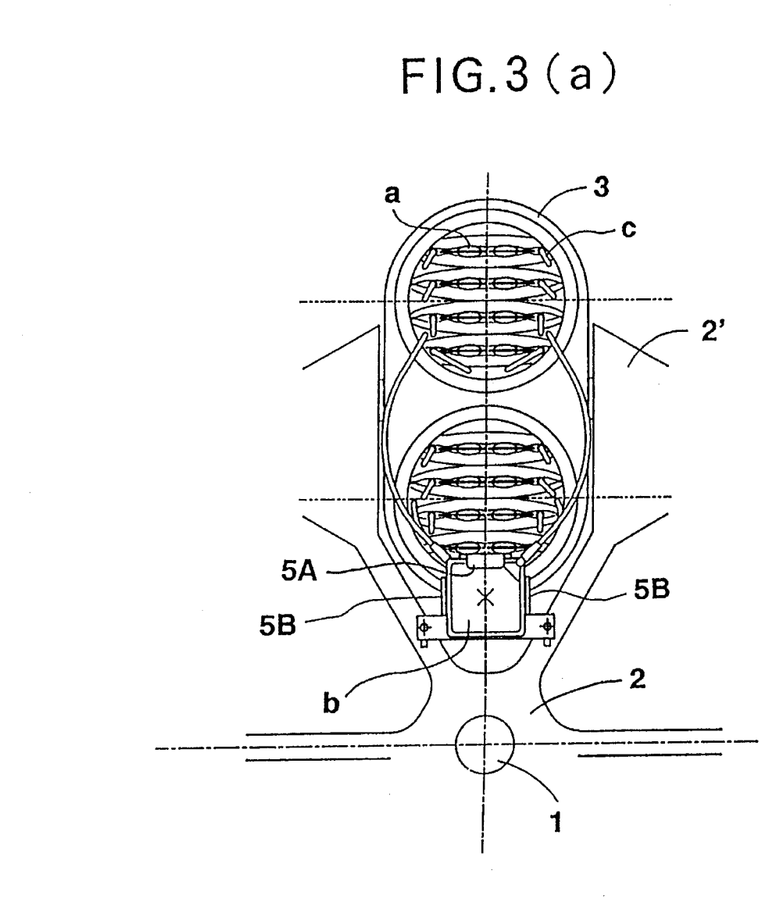
FIG. 3(a) is a partly cut-away diagrammatic plan view of another form of the centrifugal apparatus of the present invention, showing main portions thereof, which can be used in the method of the present invention, shown with two multiple blood bag units inserted in a centrifuge bucket swingably held between neighboring arms of the rotor, and shown with two leukocyte-removing filter devices placed outside of the centrifuge bucket and secured to the rotor by means of double filter device-securing means.
Figure 5A:
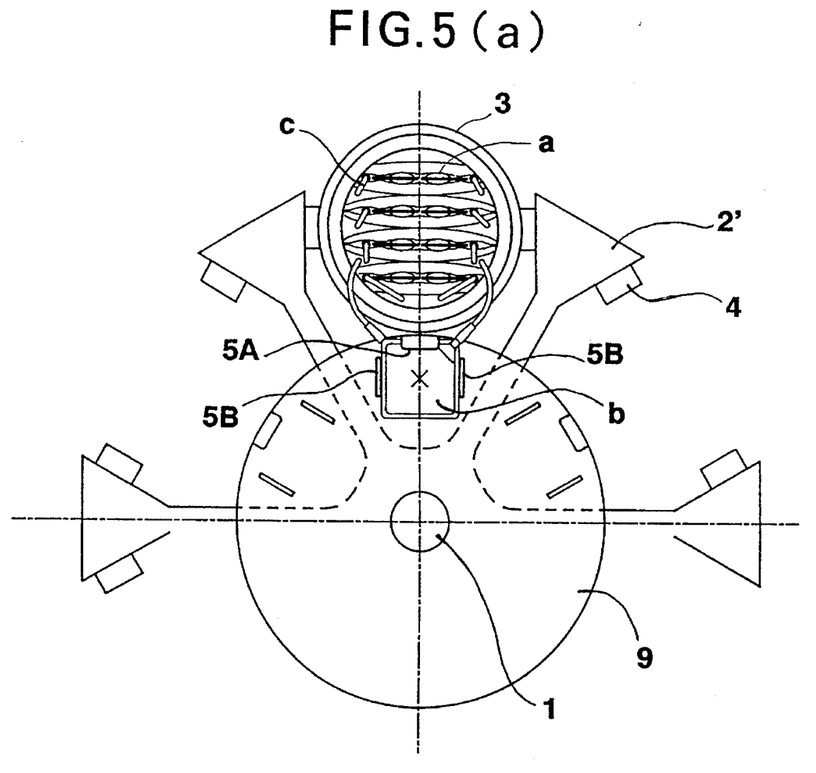
FIG. 5(a) is a partly cut-away diagrammatic plan view of still another form of the centrifugal apparatus of the present invention, showing main portions thereof, which can be used in the method of the present invention, shown with a multiple blood bag unit inserted in a centrifuge bucket swingably held between neighboring arms of the rotor, and shown with a leukocyte-removing filter device placed outside of the centrifuge bucket and indirectly secured relative to the rotor by means of a filter device-securing means provided on a peripheral portion of a rotating member (circular plate) fixedly attached to the rotation shaft.

In the present invention, the term a "center of each filter device" means a center of symmetry of the casing of the filter device excluding the blood inlet and outlet nozzles. In FIGS. 2(a), 3(a) and 5(a), the center of the filter device (b) is indicated by an X-like marking made on the filter device (b).

In the present invention, a distance of a center of the filter device from an axis of the rotation shaft is defined as a distance therebetween on a straight line drawn from the center of the filter device so as to intersect with the axis of the rotation shaft at right angles.

In step (3) of the method of the present invention, the drive motor is actuated to rotate the rotation shaft (1) and the rotor and perform separation of the blood material in the blood bag into blood components by centrifugation.

In one preferred embodiment of the method of the present invention, the at least two centrifuge bucket-holding extensions (2') include arms (2') which are substantially equal in length and radially extend from the central body portion (2) of the rotor, and each centrifuge bucket (3) is swingably attached to arms (2'). Further, in this case, each of arms (2') may have a forked free end portion including a couple of fingers, and the centrifuge buckets (3) may be pivotally held between the fingers (this embodiment is not shown in the accompanying drawings).

In another preferred embodiment of the method of the present invention, as shown in FIGS. 2(a), 3(a), 5(a) and 6, the at least two centrifuge bucket-holding extensions (2') include at least three arms (2'), and each centrifuge bucket (3) is individually, pivotally held between neighboring arms (2').

In still another preferred embodiment of the method of the present invention, the at least two bucket-holding extensions (2') include an annular extension extending from an entire periphery of the central body portion (2), and the annular extension has at least two holes for individually receiving and swingably securing each centrifuge bucket (3) at an inner circumference of each hole, the at least two holes being arranged substantially along the periphery of the annular extension (this embodiment is not shown in the accompanying drawings).

In the present invention, when the centrifuge bucket-holding extensions (2') include arms (2'), the number of arms (2') is not particularly limited. However, the number of arms (2') is generally in the range from 6 to 8.

In the present invention, when the centrifuge bucket-holding extensions (2') include arms (2'), it is preferred that arms (2') extend from the central body portion (2) at appropriate intervals allowing the center of gravity of the rotor to be positioned at a geometrical center (rotation center) of the rotor during rotation of the rotor including arms (2'), so that a weight balance of the rotor can be maintained during rotation of the rotor.

In a further preferred embodiment of the method of the present invention, each filter device (b) is directly secured to the rotor, and a center of each filter device (b) is located substantially in a plane containing a central axis passing through a bottom of the centrifuge bucket (3) and an axis of the rotation shaft (1).

Figure 4:
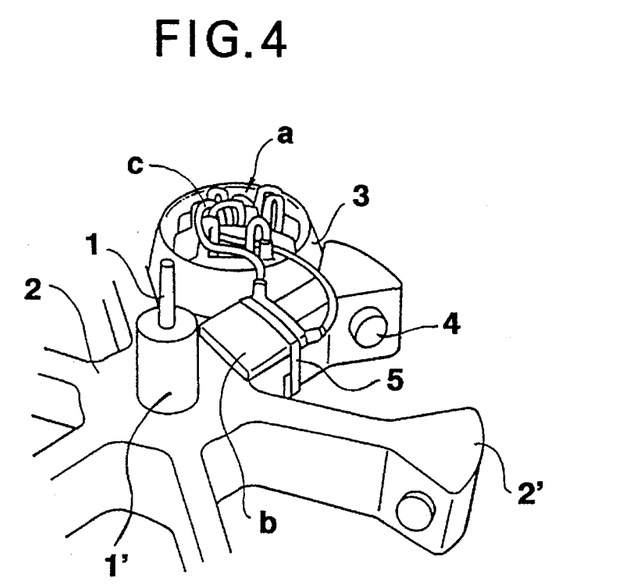
FIG. 4 is a partly cut-away diagrammatic perspective view of still another form of the centrifugal apparatus, showing main portions thereof, which can be used in the method of the present invention, shown with a multiple blood bag unit inserted in a centrifuge bucket swingably held between neighboring arms of the rotor, and shown with a leukocyte-removing filter device placed outside of the centrifuge bucket and directly secured to the rotor by means of an adhesive tape.

In the method of the present invention, each filter device (b) may be directly secured to the rotor by means of, for example, an adhesive tape as shown in FIG. 4.

Figure 2B:
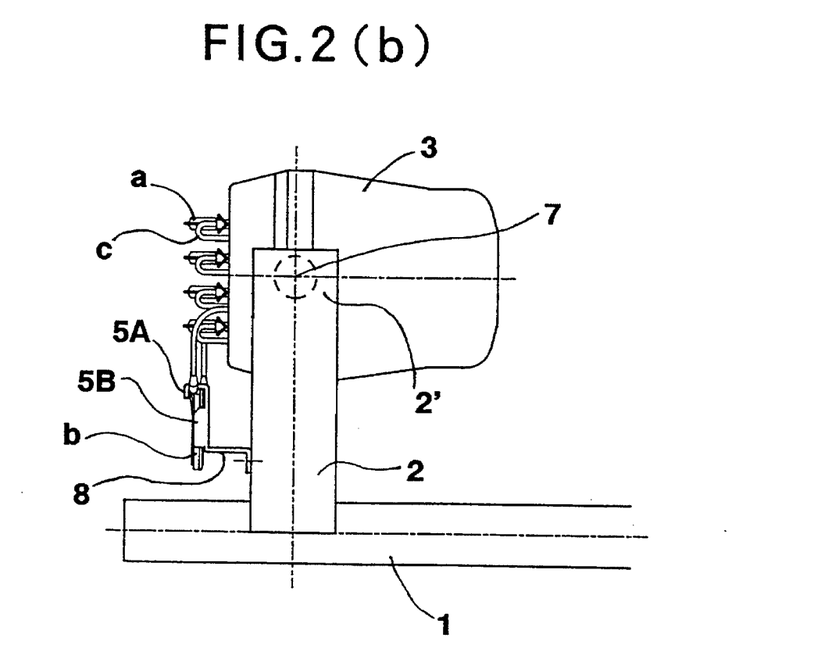
FIG. 2(b) is a partly cut-away diagrammatic side view of the apparatus shown in FIG. 2(a), which illustrates the state in which the filter device-securing means is indirectly attached to the rotor through a support leg.
Figure 3B:
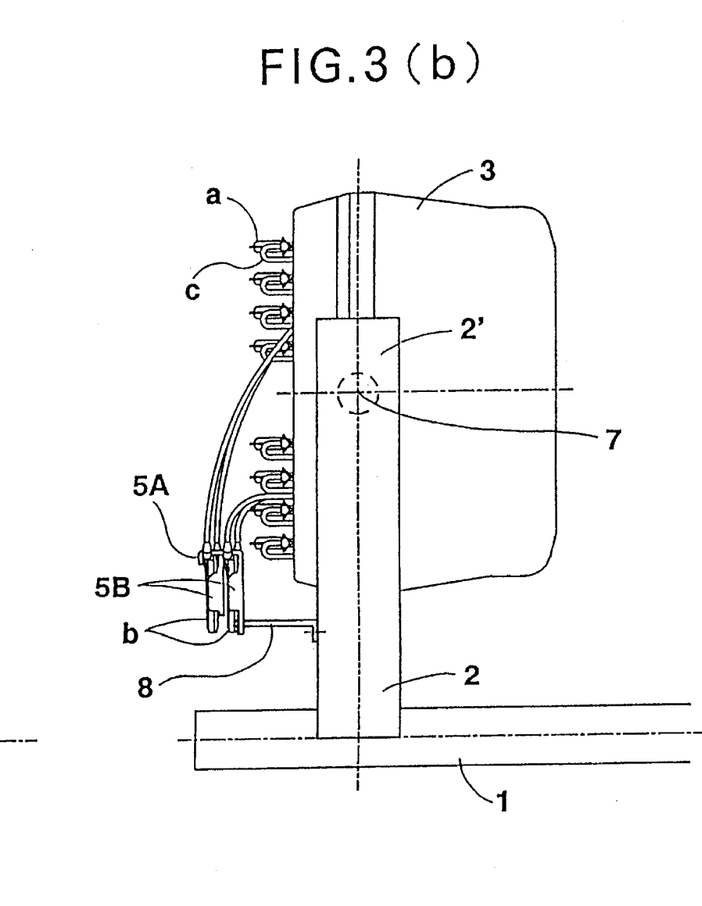
FIG. 3(b) is a partly cut-away diagrammatic side view of the apparatus shown in FIG. 3(a), which illustrates the state in which the double filter device-securing means is indirectly attached to the rotor through a pair of support legs.

In the method of the present invention, as shown in FIGS. 2(b) and 3(b), each filter device (b) may be indirectly secured to the rotor through a support (8) provided on the rotor, and a center of each filter device (b) may be located substantially in a plane containing a central axis passing through a bottom of the centrifuge bucket (3) and an axis of the rotation shaft (1).

In still a further preferred embodiment of the method of the present invention, each filter device (b) is indirectly secured relative to the rotor, and the filter device (b) is secured to a rotating member (9 and 10, 5E) fixedly attached to the rotation shaft (1) substantially in parallel with the rotor on a side of an opening of each centrifuge bucket (3) in a stationary state of the rotation shaft (1) and rotatable along with the rotor, and a center of each filter device (b) is located substantially in a plane containing a central axis passing through a bottom of the centrifuge bucket (3) and an axis of the rotation shaft (1).

Figure 5B:
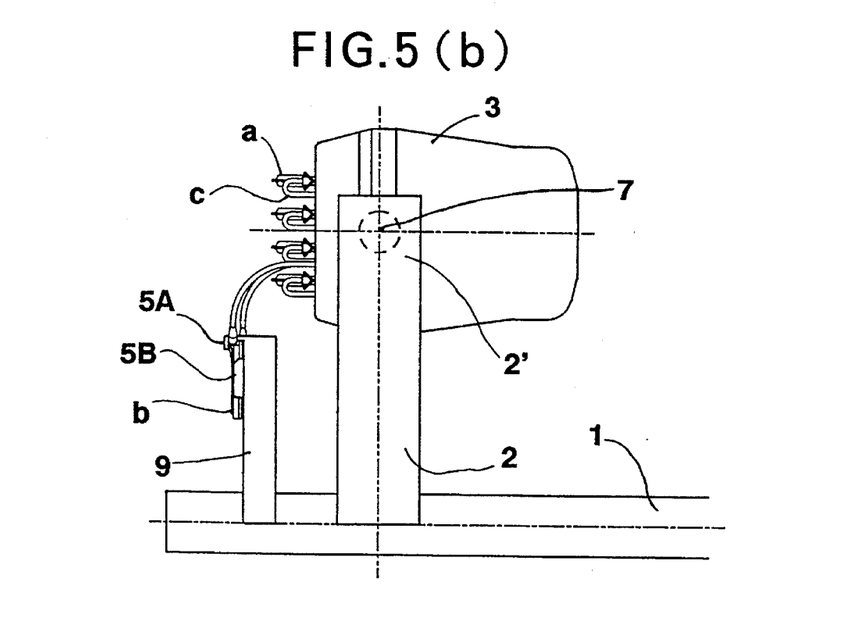
FIG. 5(b) is a partly cut-away diagrammatic side view of the apparatus shown in FIG. 5(a), which shows the state in which the filter device is secured to the circular plate fixedly attached to the rotation shaft substantially in parallel with the rotor on a side of an opening of the centrifuge bucket.
Figure 6:
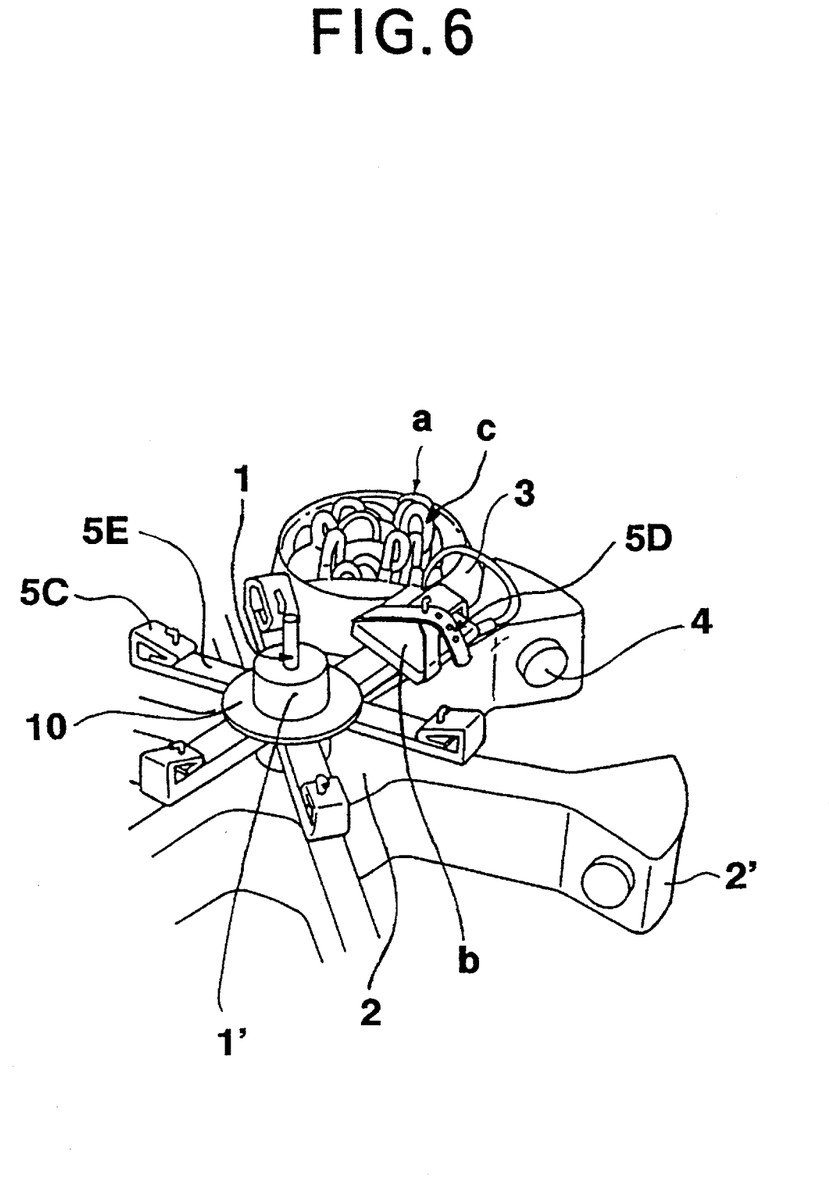
FIG. 6 is a partly cut-away diagrammatic perspective view of a further form of the centrifugal apparatus of the present invention, showing main portions thereof, which can be used in the method of the present invention, shown with a multiple blood bag unit inserted in a centrifuge bucket swingably held between neighboring arms of the rotor, and shown with a leukocyte-removing filter device placed outside of the centrifuge bucket and indirectly secured relative to the rotor by means of a filter device-securing means provided on a plurality of segments radially extending from a rotating member fixedly attached to the rotation shaft.

As shown in FIGS. 5(a) and 5(b), the above-mentioned rotating member may include a plate (9) having at least two filter device-securing means [5(5A and 5B, 5B)], and the at least two filter device-securing means [5(5A and 5B, 5B)] may be arranged substantially along a peripheral portion thereof. Alternatively, as shown in FIG. 6, the above-mentioned rotating member (10) may have at least two segments (5E) radially extending therefrom and each having filter device-securing means (5C, 5D).

In step (2) of the method of the present invention, in addition to the filter device, a blood bag or blood bags other than the blood bag containing the blood material may also be placed outside of the centrifuge bucket (3) and be directly or indirectly secured relative to the rotor. In this case, if desired, a center of the blood bag or bags not containing a blood material and placed outside of the centrifuge bucket (3) can be located at a distance from an axis of the rotation shaft (1) which is smaller than a distance between a pivotal axis (7) of the turning of the centrifuge bucket (3) and an axis of the rotation shaft (1) at a portion thereof which has the rotor connected thereto.

By the centrifugation effected in step (3) of the method of the present invention, the blood material, (for example, whole blood) is separated into an upper layer composed of plasma component and a lower layer composed of a red cell concentrate (which contains leukocytes when the original blood material contains leukocytes). (When the centrifugal force is relatively large, the plasma obtained is platelet-poor plasma, whereas when the centrifugal force is relatively small, the plasma obtained is platelet-rich plasma.)

After completion of step (3) of the method of the present invention, leukocytes are filtered from the blood component (red cell concentrate) separated in step (3) from the blood material, using the filter device of the multiple blood bag unit, to obtain a leukocyte-removed blood product (red cell concentrate).

In the method of the present invention, it is preferred that the location at which the filter device is directly or indirectly secured relative to the rotor, be selected so as to ensure that the filter device does not contact the centrifuge bucket and the blood bags inserted therein both when the rotor is in a stationary state and when the centrifuge bucket is turned and oriented substantially in a direction of a centrifugal force exerted when the rotor is rotated.

In the present invention, from the viewpoint of reducing a centrifugal force to be sustained by the filter device, it is preferred that the distance between an axis of the rotation shaft and a center of the filter device secured relatively to the rotor be as small as possible.

In another aspect of the present invention, there is provided a centrifugal apparatus for centrifuging a blood material collected in a multiple blood bag unit to thereby separate the blood material into blood components, comprising:

a rotation shaft to be connected to a drive motor;

a rotor fixedly connected at a central portion thereof to the rotation shaft and rotatable in accordance with rotation of the rotation shaft, the rotor comprising a central body portion and at least two centrifuge bucket-holding extensions radially extending from the central body portion;

at least two centrifuge buckets each for accommodating therein at least one blood bag of a multiple blood bag unit including a plurality of flexible blood bags liquid-tightly connected to at least one leukocyte-removing filter device through flexible tubes in a predetermined order, at least the filter device being adapted to be placed outside of the centrifuge bucket, each centrifuge bucket being swingably attached to the centrifuge bucket-holding extensions of the rotor, wherein the centrifuge bucket is adapted to be turned and oriented substantially in a direction of a centrifugal force exerted when the rotor is rotated; and at least two filter device-securing means each for individually securing the filter device of each multiple blood bag unit directly or indirectly to the rotor, a center of each filter device-securing means being located at a distance from an axis of the rotation shaft which is smaller than a distance between a pivotal axis of the turning of the centrifuge bucket and an axis of the rotation shaft at a portion thereof which has the rotor connected thereto.

The centrifugal apparatus of the present invention can be advantageously used in the method of the present invention.

In the apparatus of the present invention, a center of the filter device-securing means generally corresponds to a center of the filter device secured by the filter device-securing means.

There is no particular limitation with respect to the materials for various components of the centrifugal apparatus of the present invention, such as a rotation shaft (1), a cylindrical reinforcing member (1') provided around and secured to the rotation shaft (1), a rotor, arms (2'), pivot pins (4) and centrifuge buckets (3). For producing these components, customary materials for such components used in a conventional centrifugal apparatus can be used. That is, the above-mentioned components can be made of, for example, metals having a satisfactory strength, such as iron (e.g. a stainless steel and a soft iron) and aluminum.

When the filter device-securing means (5A, 5B and 5C, 5D) is to be provided on a rotating member (9, and 10, 5E) fixedly attached to the rotation shaft (1) substantially in parallel with the rotor, the above-mentioned customary materials can also be used for producing the rotating member.

With respect to the material for the filter device-securing means, there is no particular limitation. Examples of materials for the filter device-securing means include metals (e.g., iron and aluminum) and resins. From the viewpoint of improved protection of the filter device, it is preferred that the filter device-securing means be made of a resilient material (having cushioning properties) at least at a portion of the filter device-securing means which contacts the filter device. Examples of resilient materials include a polyurethane, a rubber, a resin and the like. Other examples include a foamed material and a mass of a fibrous material each produced from various customary materials.

BEST MODE FOR CARRYING OUT THE INVENTION

The present invention will be described in greater detail with reference to the following embodiments, which should not be construed as limiting the scope of the present invention.

FIGS. 2(a) and 2(b) illustrate a first embodiment of the present invention. That is, FIG. 2(a) is a partly cut-away diagrammatic plan view of one form of the centrifugal apparatus of the present invention, showing main portions thereof, which can be used in the method of the present invention. A plurality of blood bags a of a multiple blood bag unit are inserted in centrifuge bucket 3 pivotally held between neighboring arms 2', 2' of the rotor, while leukocyte-removing filter device b is placed outside of centrifuge bucket 3 and secured to central body portion 2 of the rotor by means of filter device-securing means 5 (5A and 5B, 5B). FIG. 2(b) is a partly cut-away diagrammatic side view of the apparatus shown in FIG. 2(a), which illustrates the state in which filter device-securing means 5 (5A and 5B, 5B) is indirectly attached to central body portion 2 of the rotor through support leg 8.

In the first embodiment of the present invention, with respect to the multiple blood bag unit including blood bags a liquid-tightly connected to filter device b through flexible tubes c, only flexible blood bags a and flexible tubes c are accommodated in centrifuge bucket 3, the blood bags being disposed vertically to a bottom of centrifuge bucket 3, as in the case of using a conventional multiple blood bag unit consisting of only flexible blood bags liquid-tightly connected through flexible tubes. Filter device b is placed outside of centrifuge bucket 3 along with portions of a couple of tubes attached thereto.

When tubes c has a chamber and/or a clip attached thereto in intermediate portions thereof, they are also accommodated in centrifuge bucket 3 along with flexible tubes c. (the chambers are for facilitating escape of air from the tubes and for measuring a blood flow rate, and the clip is for control of a blood flow rate.) It is preferred that a bag containing a blood material and a bag containing a reagent, such as an anticoagulant, be accommodated in centrifuge bucket 3 so as to be covered by empty bags to protect the bags containing a blood material and a reagent. The tubes are made up into a bundle without causing any significant tension, wound and appropriately inserted between the blood bags. The blood bags have junctions at which the blood bags are connected to the tubes. Such junctions are most likely to be damaged and, therefore, it is preferred that the blood bags be accommodated in the centrifuge buckets so that the junctions are located near an opening of the centrifuge bucket, thereby preventing the junction from a danger of contacting with the inner wall of the centrifuge bucket.

The filter device-securing means comprises a quadrilateral plate (made of, for example, stainless steel or the like), and wherein the plate is attached to central body portion 2 of the rotor through support leg 8 (which is mentioned below).

In the quadrilateral plate, one side (remote from the rotation shaft) of a pair of opposite sides, which are in parallel with the pivotal axis of centrifuge bucket 3, has at its central portion a protrusion which protrudes upwardly of the side. The protrusion has a top end portion thereof bent perpendicularly thereto and inwardly of the side, so that U-shaped recess 5A sufficient to fittedly receive one end of a flat casing of filter device b is formed. The other side opposite to the side having U-shaped recess 5A has support leg 8 extending downwardly of the opposite side edge, wherein support leg 8 has a foot used for securely attaching support leg 8 to central body portion 2 of the rotor by means of a screw or the like.

Respective sides of another pair of opposite sides have, at central portions thereof, protrusions 5B, 5B protruding upwardly of both sides.

In securing the filter device, flat filter device b is inserted between opposite protrusions 5B, 5B of the rectangular plate, and the forward end of filter device b is fittedly received by U-shaped recess 5A. U-shaped recess 5A serves to securely hold filter device b against a centrifugal force to be exerted when the rotor is rotated, and opposite protrusions 5B, 5B serve to prevent filter device b from lateral displacement. Thus, secure engagement of filter device b with filter device-securing means 5 (5A and 5B, 5B) is established.

Alternatively, filter device-securing means 5 (5A and 5B, 5B) can be provided directly on the upper surface of the rotor. However, it is preferred that, as in this embodiment, filter device-securing means be provided indirectly on central body portion 2 of the rotor through support leg 8 at the same level as the level of the top of blood bags a. As shown in FIGS. 2(a) and 2(b), it is preferred that filter device-securing means is provided at a location such that a center of each filter device-securing means be located substantially in a plane containing a central axis passing through a bottom of centrifuge bucket 3 and an axis of rotation shaft 1. Due to the location of filter device-securing means 5 (5A and 5B, 5B) as described above, it becomes possible to avoid the danger of causing flexible tubes c (connecting filter device b placed outside of centrifuge bucket 3 with blood bags a of the multiple blood bag unit in centrifuge bucket 3) to be bent at an acute angle under a centrifugal force during the operation of centrifugation and damaged.

FIGS. 3(a) and 3(b) illustrate a second embodiment of the present invention. That is, FIG. 3(a) is a partly cut-away diagrammatic plan view of another form of the centrifugal apparatus of the present invention, showing main portions thereof, which can be used in the method of the present invention. A plurality of blood bags a of each of two multiple blood bag units are inserted in centrifuge bucket 3 pivotally held between neighboring arms 2', 2' of the rotor, while two leukocyte-removing filter devices b, b are placed outside of centrifuge bucket 3 and secured to the rotor by means of double filter device-securing means 5 (5A and 5B, 5B). FIG. 3(b) is a partly cut-away diagrammatic side view of the apparatus shown in FIG. 3(a), which illustrates the state in which the double filter device-securing means 5 (5A and 5B, 5B) is indirectly attached to the respective base portions of arms 2', 2' of the rotor through a pair of support legs 8, 8.

Double filter device-securing means 5 (5A and 5B, 5B) shown in FIGS. 3(a) and 3(b) comprises upper and lower plates each for securing a filter device thereto. Each of the upper and lower plates has substantially the same configuration as that of the quadrilateral plate of the centrifugal apparatus shown in FIGS. 2(a) and 2(b). The lower plate is attached to neighboring arms 2', 2' of the rotor through a pair of support legs 8, 8 (which is mentioned below) in a bridging manner.

In the lower plate, one side (remote from the rotation shaft) of a pair of opposite sides, which are in parallel with the pivotal axis of centrifuge bucket 3, has at its central portion a protrusion. The protrusion protrudes upwardly of the side and has a top end portion thereof bent perpendicularly thereto and inwardly of the side. The bending of the top end portion of the protrusion is effected so as to allow a couple of filter devices with the upper plate positioned therebetween to be accommodated in a preliminary U-shaped recess formed by the bending. The upper plate of the filter device-securing means is welded to the inner wall of the preliminary U-shaped recess-forming protrusion at a middle portion thereof in a manner such that the upper plate is disposed in parallel with the lower plate, thus forming upper and lower U-shaped recesses. That is, upper U-shaped recess 5A sufficient to fittedly receive one end of a flat casing of first filter device b is formed, and a lower U-shaped recess sufficient to fittedly receive one end of a flat casing of second filter device b is also formed.

In each of the upper and lower plates, respective sides of another pair of opposite sides have, at central portions thereof, protrusions 5B, 5B protruding upwardly thereof for inserting filter device b therebetween as in the first embodiment of the present invention.

As seen from FIG. 3(b), both upper and lower plates have substantially the same configuration, except that the lower plate has, on a side opposite to the lower U-shaped recess-having side, an extension integrally formed therewith and extending therefrom. The extension has lugs projecting from both sides as seen from FIG. 3(a). That is, the lower plate has a  shape on a whole, differing from the upper plate has a completely quadrilateral shape. Support legs 8, 8 are fixed to both lugs and extend downwardly of the lugs, and each of support legs 8, 8 has a foot used for securely attaching support leg 8 to a base portion of arm 2' by means of a screw or the like. Thus, the double filter device-securing means is attached to the base portions of arms 2', 2' in a bridging manner.

In the second embodiment shown in FIGS. 3(a) and 3(b), centrifuge bucket 3 has a structure such that it can accommodate two multiple blood bag units therein.

Secure engagement of the couple of filter devices b, b with the double filter device-securing means can be performed in the same manner as in the first embodiment.

FIG. 4 illustrates a third embodiment of the present invention. That is, FIG. 4 is a partly cutaway diagrammatic perspective view of still another form of the centrifugal apparatus, showing main portions thereof, which can be used in the method of the present invention. A plurality of blood bags a of a multiple blood bag unit are inserted in centrifuge bucket 3 pivotally held between neighboring arms 2', 2' of the rotor, while leukocyte-removing filter device b is placed outside of centrifuge bucket 3 and directly secured to the rotor by means of adhesive tape 5.

As can be easily understood from the above, in the third embodiment of the present invention, the centrifugal apparatus itself has not any specific filter device-securing means originally attached thereto, and a separate appropriate filter device-securing means is used.

This embodiment is advantageous in that any types of conventional centrifugal apparatuses can be used, and a filter device can be very readily secured irrespective of the shape thereof. Further, an adhesive tape is cheap and can be easily obtained. However, in this third embodiment of the present invention, the location of filter device b should be carefully selected so as not to cause flexible tubes c (connecting filter device b to blood bags a) to be sharply bent at an acute angle and damaged under a centrifugal force to be exerted when the rotor is rotated. In addition, the operation of removing adhesive tape 5 is cumbersome, and it is likely that, even after the centrifugation operation is completed and the filter device is released from the securing to the rotor, the adhesive portion of adhesive tape 5 remains unremoved on the surface of filter device b or arm 2'. For the above reasons, a rubber belt which is of the same type as that shown in FIG. 6 (which is mentioned below) can also be advantageously utilized in place of the adhesive tape.

When band-type securing means, for example, the above-mentioned adhesive tape or rubber belt, is used, the filter device should be appropriately secured to the arm so as to prevent the filter device from being displaced in a centrifugal direction under a centrifugal force to be exerted during the operation of centrifugation.

FIGS. 5(a) and 5(b) illustrate a fourth embodiment of the present invention. That is, FIG. 5(a) is a partly cut-away diagrammatic plan view of still another form of the centrifugal apparatus of the present invention, showing main portions thereof, which can be used in the method of the present invention. A plurality of blood bags a of a multiple blood bag unit are inserted in centrifuge bucket 3 pivotally held between neighboring arms 2', 2' of the rotor, while leukocyte-removing filter device b is placed outside of centrifuge bucket 3 and indirectly secured relative to the rotor by means of filter device-securing means 5 (5A and 5B, 5B) provided on a peripheral portion of rotating member 9 (circular plate) fixedly attached to rotation shaft 1. FIG. 5(b) is a partly cut-away diagrammatic side view of the apparatus shown in FIG. 5(a), which illustrates the state in which filter device-securing means b is provided on circular plate 9 fixedly attached to rotation shaft 1 substantially in parallel with the rotor on a side of an opening of the centrifuge bucket 3.

The same number of filter device-securing means 5 (5A and 5B, 5B) as the number of filter devices b are provided on the upper flat surface of circular plate 9 substantially along a periphery thereof, wherein a center of each filter device b is located substantially in a plane containing a central axis passing through a bottom of centrifuge bucket 3 and an axis of rotation shaft 1. In this embodiment, circular plate 9 is fixedly attached to rotation shaft 1 at a location such that the filter device be positioned at the same level as the level of top of blood bags a.

The filter device-securing means in this embodiment comprises U-shaped recess 5A and a pair of opposite protrusions 5B, 5B provided on circular plate 9.

The above U-shaped recess is provided as follows. Circular plate 9 has a protrusion which protrudes upwardly of a portion of the periphery of circular plate 9 in parallel with the pivotal axis of centrifuge bucket 3 and has a top end portion thereof bent perpendicularly thereto and inwardly of the periphery of circular plate 9 as depicted in FIG. 5(a), so that a U-shaped recess sufficient to fittedly receive one end of a flat casing of filter device b is formed. Each of opposite protrusions 5B, 5B comprises a protrusion which protrudes upwardly and vertically of the upper flat surface of circular plate 9, wherein each of opposite protrusion 5B, 5B extends perpendicularly to the direction of extension of U-shaped recess 5A.

In securing the filter device, the flat filter device b is inserted between opposite protrusions 5B, 5B, and the forward end of the filter device b is fittedly received by U-shaped recess 5A. U-shaped recess 5A serves to securely hold filter device b against centrifugal force, and opposite protrusions 5B, 5B serve to prevent filter device b from lateral displacement. Thus, secure engagement of the filter device with the filter device-securing means is established.

The above-mentioned opposite protrusions 5B, 5B can be constructed to have a slide mechanism so that the distance between opposite protrusions 5B, 5B is variable. With such a construction, filter devices of various sizes can be secured to circular plate 9 between opposite protrusions 5B, 5B.

This fourth embodiment is advantageous in that the centrifugal apparatus of this embodiment can be prepared simply by additionally attaching a rotating member to the rotation shaft of a conventional apparatus, and the upper surface of the rotor can be free from any projections, so that the operations, such as attaching of a centrifuge bucket to the rotor of the apparatus, can be readily performed.

In the embodiment shown in FIGS. 5(a) and 5(b), the rotating member has a disk-type configuration. However, there is particularly no limitation with respect to the shape of a rotating member insofar as the filter device can be stably secured thereto and a weight balance is maintained during rotation of the rotation shaft 1.

FIG. 6 illustrates a fifth embodiment of the present invention. That is, FIG. 6 is a partly cut-away diagrammatic perspective view of a further form of the centrifugal apparatus of the present invention, showing main portions thereof, which can be used in the method of the present invention. A plurality of blood bags a of a multiple blood bag unit are inserted in centrifuge bucket 3 pivotally held between neighboring arms 2', 2' of the rotor, while leukocyte-removing filter device b is placed outside of centrifuge bucket 3 and indirectly secured relative to the rotor by means of filter device-securing means 5 (5C, 5D) provided on a plurality of segments 5E radially extending from disk 10 fixedly attached to rotation shaft 1.

Disk 10 has, at lower flat surface thereof, grooves to engagingly receive end portions of segments 5E therein, wherein each of segments 5E is fixed to disk 10 by means of, for example, as adhesive or the like. Disk 10 is securely attached to rotation shaft 1 by means of upper and lower reinforcing members 1' and 1' through thread-engagement techniques ordinarily used in the art.

Each of segments 5E has at its end portion an engaging portion, wherein clip 5C serves to resiliently, securely hold the forward end of the casing of leukocyte-removing filter device b. Clip 5C has a hook on the upper surface thereof, which serves to secure rubber belt 5D in a state in which rubber belt 5D is wound around filter device b, as depicted in FIG. 6.

As still a further embodiment of the centrifugal apparatus of the present invention, there can be mentioned a centrifugal apparatus in which an elongated recess is formed in an upper portion of the arm to accommodate and securely hold a filter device therein (not shown). In this embodiment, in order to secure the filter device more firmly, an appropriate type of securing means can be applied, such as the above-mentioned adhesive tape and band-type securing means. With respect to the configuration of the elongated recess, there can be mentioned an example in which a recess is formed in the arm so that the recess extends perpendicularly to a longitudinal axis of the arm and so that the filter devise is inserted in the recess so as to extend downwardly, longitudinally along the depth of the recess. In this example, the centrifugal force substained by different portions of the filter device can be rendered uniform. However, this example has a disadvantage in that the arm has limited durability. Therefore, alternatively, there can be mentioned another example in which a recess is formed so that the recess extends along a longitudinal axis of the arm and so that the filter device is inserted so as to lay itself along the length of the arm. This example is advantageous not only in that the arm can be durable, but also in that this technique is advantageously applicable when the filter device is relatively small in size and has a flat configuration.

In operation of the centrifugal apparatus of the present invention, a plurality of multiple blood bag units each including a plurality of blood bags (at least one of which contains a blood material) connected to at least one leukocyte-removing filter device are provided, and at least the blood material-containing blood bag or bags of each multiple blood bag unit is inserted in each of a plurality of centrifuge buckets securely attached to the rotor, while placing at least the leukocyte-removing filter device outside of the centrifuge buckets and securing the filter device relative to the rotor. In this instance, a care must be paid with respect to the arrangement of the multiple blood bag units in the apparatus so that a weight balance of the whole apparatus loaded with the multiple blood bag units can be maintained during rotation of the rotor. Next, a drive motor connected to the rotation shaft of the rotor of the apparatus is actuated to rotate the rotor and perform separation of the blood materials in the blood bags into blood components by centrifugation. Operation conditions including a rotation time and a rotation rate are appropriately selected from those ordinarily employed for separating a blood material into blood components. Generally, the centrifugation is carried out under about 1,000 to about 4,000 G for about 10 to about 15 minutes.

Upon completion of the separation of blood materials into blood components, the leukocyte-removing filter device securely attached to the rotor through the filter device-securing means is released, and then, the blood bags are taken out gently from the centrifuge buckets.

In the centrifugal separation by the method and apparatus of the present invention, a centrifugal force exerted on the leukocyte-removing filter device during the operation of centrifugation is still considerably large. Accordingly, when an area of contact between the leukocyte-removing filter device and a portion of the filter device-securing means which engages the filter device is small, the filter device tends to suffer an extremely large pressure at a portion thereof which contacts the engaging portion of the filter device-securing means, leading to a damaging or breakage of the filter device. Therefore, it is preferred to protect the filter device at a portion thereof which contacts the engaging means of the filter device-securing means. For the purpose of protecting the leukocyte-removing filter device, there can be employed, for example, a method in which the filter device is wrapped with a cushioning material, such as a non-woven fabric or a sponge and then, is brought into engagement with the engaging portion of the filter device-securing means; or a method in which the engaging portion of the filter device-securing means is preliminarily provided with a cushioning member, such as a member made of a polyurethane or rubber material, at a face thereof which will contact the filter device and then, is used for engaging the filter device at the face having the cushioning member. In this manner, it becomes possible that the filter device is indirectly contacted with the filter device-securing means at areas thereof as large and as many as possible, thus enabling the filter device to be subjected to centrifugation under safety conditions.

The above description of the method and apparatus of the present invention is directed mainly to the embodiments using a multiple blood bag unit containing a flat leukocyte-removing filter device. However, the above description is not construed as limiting the present invention, and it will be easily understood to those skilled in the art that the present invention may also be practiced with respect to leukocyte-removing filter devices of other shapes, such as a cylindrical shape, etc.

What is claimed is:

1. A method for separating a blood material into blood components by centrifugation, comprising the steps of:

(1) providing at least two multiple blood bag units each including a plurality of flexible blood bags liquid-tightly connected to at least one leukocyte-removing filter device through flexible tubes in a predetermined order, at least one of said flexible blood bags containing a blood material, and providing a centrifugal apparatus including a rotation shaft connected to a drive motor, a rotor fixedly connected at a central portion thereof to said rotation shaft and rotatable in accordance with rotation of said rotation shaft, said rotor including a central body portion and at least two centrifuge bucket-holding extensions radially extending from said central body portion, and at least two centrifuge buckets each swingably attached to said centrifuge bucket-holding extensions of the rotor, wherein said centrifuge bucket is adapted to be turned and oriented substantially in a direction of a centrifugal force exerted when said rotor is rotated;

(2) inserting at least said at least one flexible blood bag, which contains a blood material, of said plurality of flexible blood bags of each multiple blood bag unit in each centrifuge bucket while placing at least said at least one leukocyte-removing filter device of said plurality of flexible blood bags and said at least one leukocyte-removing filter device of each multiple blood bag unit outside of each centrifuge bucket, wherein said filter device is directly or indirectly secured to said rotor, or indirectly secured to said rotation shaft, and wherein a center of each filter device is located at a distance from an axis of said rotation shaft which is smaller than a distance between a pivotal axis of the turning of said centrifuge bucket and an axis of said rotation shaft at a portion thereof which has said rotor connected thereto; and (3) actuating said drive motor to rotate said rotation shaft and said rotor and perform separation of said blood material in said blood bag into blood components by centrifugation.

2. The method according to claim 1, wherein said at least two centrifuge bucket-holding extensions include arms which are substantially equal in length and radially extend from said central body portion of the rotor, and wherein each centrifuge bucket is swingably attached to said arms.

3. The method according to claim 1, wherein said at least two centrifuge bucket-holding extensions include at least three arms, and wherein each centrifuge bucket is individually, pivotally held between neighboring arms.

4. The method according to any one of claims 1 to 3, wherein each filter device is directly secured to said rotor, and wherein a center of each filter device is located substantially in a plane containing a central axis passing through a bottom of said centrifuge bucket and an axis of said rotation shaft.

5. The method according to any one of claims 1 to 3, wherein each filter device is indirectly secured to said rotor through a support securely attached onto said rotor, and wherein a center of each filter device is located substantially in a plane containing a central axis passing through a bottom of said centrifuge bucket and an axis of said rotation shaft.

6. The method according to any one of claims 1 to 3, wherein each filter device is indirectly secured to said rotation shaft through a rotating member fixedly attached to said rotation shaft, wherein said filter device is secured to said rotating member substantially in parallel with said rotor on a side of an opening of each centrifuge bucket in a stationary state of said rotation shaft and rotatable along with said rotor, and wherein a center of each filter device is located substantially in a plane containing a central axis passing through a bottom of said centrifuge bucket and an axis of said rotation shaft.

7. The method according to claim 6, wherein said rotating member has at least two segments radially extending therefrom and each having filter device-securing means.

8. The method according to claim 6, wherein said rotating member includes a plate having at least two filter device-securing means, and wherein said at least two filter device-securing means are arranged substantially along a peripheral portion thereof.

9. The method according to claim 1, wherein said blood material is a leukocyte-containing blood material.

10. A centrifugal apparatus for centrifuging a blood material collected in a multiple blood bag unit to thereby separate said blood material into blood components, comprising:

a rotation shaft to be connected to a drive motor;

a rotor fixedly connected at a central portion thereof to said rotation shaft and rotatable in accordance with rotation of said rotation shaft, said rotor comprising a central body portion and at least two centrifuge bucket-holding extensions radially extending from said central body portion;

at least two centrifuge buckets each for accommodating therein at least one flexible blood bag of a multiple blood bag unit including a plurality of flexible blood bags liquid-tightly connected to at least one leukocyte-removing filter device through flexible tubes in a predetermined order, at least said at least one leukocyte-removing filter device being adapted to be placed outside of said centrifuge bucket, each centrifuge bucket being swingably attached to said centrifuge bucket-holding extensions to the rotor, wherein said centrifuge bucket is adapted to be turned and oriented substantially in a direction of a centrifugal force exerted when said rotor is rotated; and at least two filter device-securing means each for individually securing said filter device of each multiple blood bag unit directly or indirectly to said rotor, or indirectly to said rotation shaft, a center of each filter device-securing means being located at a distance from an axis of said rotation shaft which is smaller than a distance between a pivotal axis of the turning of said centrifuge bucket and an axis of said rotation shaft at a portion thereof which has said rotor connected thereto.

11. The centrifugal apparatus according to claim 10, wherein said at least two centrifuge bucket-holding extensions include arms which are substantially equal in length and radially extend from said central body portion of the rotor, and wherein each centrifuge bucket is swingably attached to said arms.

12. The centrifugal apparatus according to claim 11, wherein each arm has a forked free end portion including a couple of fingers, wherein said centrifuge buckets are pivotally held between said fingers.

13. The centrifugal apparatus according to claim 10, wherein said at least two centrifuge bucket-holding extensions include at least three arms, and wherein each centrifuge bucket is individually, pivotally held between neighboring arms.

14. The centrifugal apparatus according to any one of claims 10 to 13, wherein each filter device-securing means is directly provided on said rotor, and wherein a center of each filter device-securing means is located substantially in a plane containing a central axis passing through a bottom of said centrifuge bucket and an axis of said rotation shaft.

15. The centrifugal apparatus according to any one of claims 10 to 13, wherein each filter device-securing means is indirectly provided on said rotor through a support securely attached onto said rotor, and wherein a center of each filter device-securing means is located substantially in a plane containing a central axis passing through a bottom of said centrifuge bucket and an axis of said rotation shaft.

16. The centrifugal apparatus according to any one of claims 10 to 13, wherein each filter device-securing means is provided on a rotating member fixedly attached to said rotation shaft substantially in parallel with said rotor on a side of an opening of each centrifuge bucket in a stationary state of said rotation shaft and rotatable along with said rotor, and wherein a center of each filter device-securing means is located substantially in a plane containing a central axis passing through a bottom of said centrifuge bucket and an axis of said rotation shaft.

17. The centrifugal apparatus according to claim 16, wherein said rotating member has at least two segments radially extending therefrom, and wherein each segment has said filter device-securing means.

18. The centrifugal apparatus according to claim 16, wherein said rotating member includes a plate, and wherein said at least two filter device-securing means are arranged substantially along a peripheral portion thereof.

* * * * *